Figure 1:
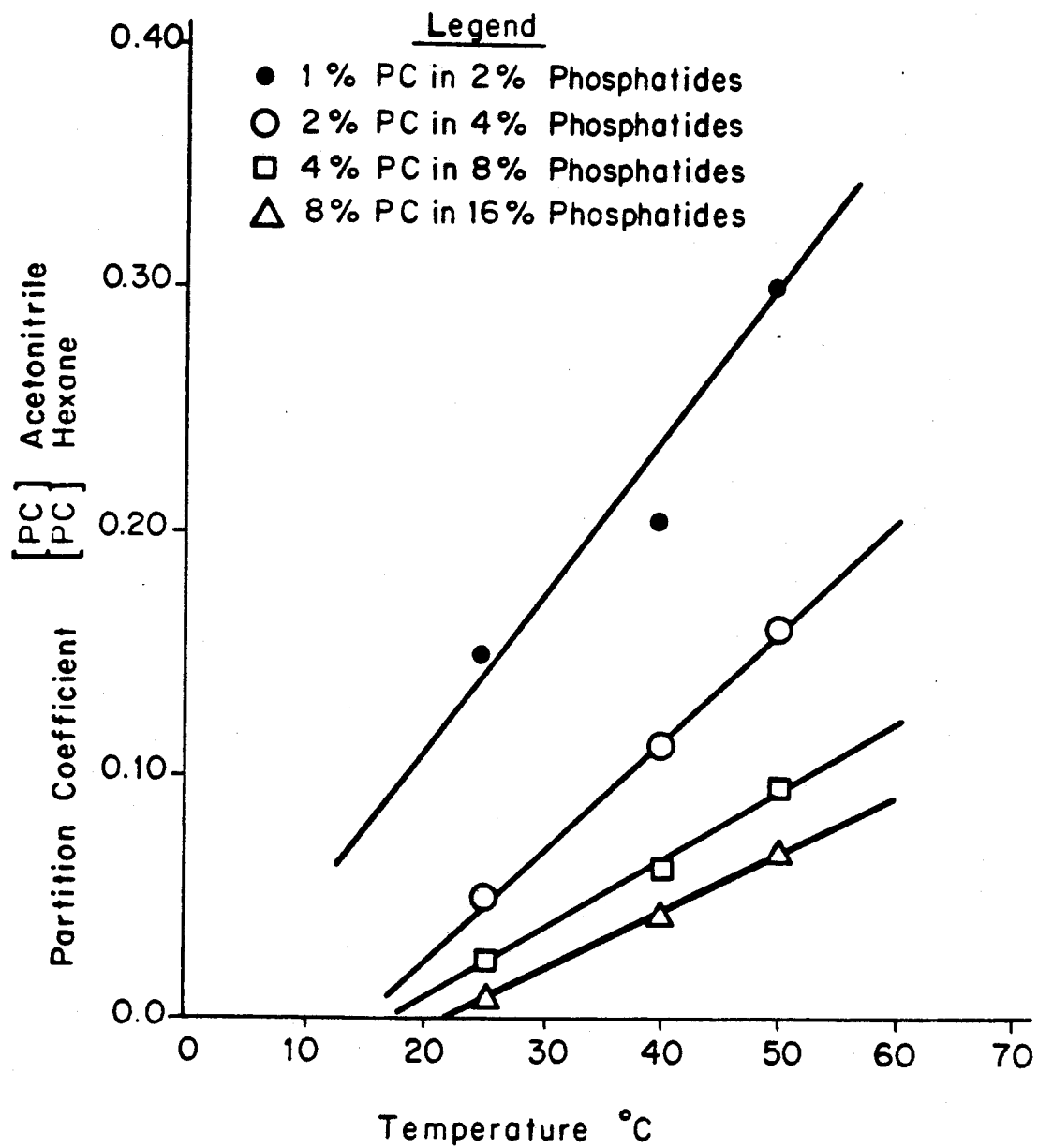

United States Patent [19]

Kearns et al.

[11] Patent Number: 5,084,215
[45] Date of Patent: * Jan. 28, 1992

[54] PROCESS FOR PURIFICATION OF PHOSPHOLIPIDS

[75] Inventors: John J. Kearns, Princeton; Paul A. Tremblay, Hamilton, both of N.J.

[73] Assignee: The Liposome Company, Inc., Princeton, N.J.

[ * ] Notice: The portion of the term of this patent subsequent to Dec. 22, 2004 has been disclaimed.

[21] Appl. No.: 260,156

[22] Filed: Oct. 20, 1988

Related U.S. Application Data

[60] Division of Ser. No. 928,508, Nov. 7, 1986, Pat. No. 4,814,111, which is a division of Ser. No. 698,668, Feb. 6, 1985, Pat. No. 4,714,571, which is a continuation-in-part of Ser. No. 579,535, Feb. 13, 1984, abandoned.

[51] Int. Cl.$^5$ ............................................. C11C 1/00
[52] U.S. Cl. ................................. 260/403; 260/412.4
[58] Field of Search .......................... 260/403, 412.4

[56] References Cited

PUBLICATIONS

Jungalwala et al, "Biochem. J." 155, 55–60 (1976).

*Primary Examiner*—J. E. Evans
*Attorney, Agent, or Firm*—Allen Bloom; Catherine L. Kurtz

[57] ABSTRACT

A process for the separation and purification of individual phospholipids, especially phosphatidylcholine or lecithin and phosphatidylethanolaine, from mixtures containing members of the sub-class of phosphatides, incorporating methods of solvent extraction appropriate to the scale of the sample and utilizing an acetonitrile, acetonitrile-hydrocarbon, or acetonitrile-fluorocarbon solvent, which exhibit differential solubility properties towards the individual phospholipids.

7 Claims, 3 Drawing Sheets

PROCESS FOR PURIFICATION OF PHOSPHOLIPIDS

This application is a division of application Ser. No. 06/928,508, filed Nov. 7, 1986, now U.S. Pat. No. 4,814,111, which in turn is a division of application Ser. No. 06/698,668, filed Feb. 6, 1985, now U.S. Pat. No. 4,714,571, which in turn is a continuation-in-part of application Ser. No. 06/579,535, filed Feb. 13, 1984, now abandoned.

TABLE OF CONTENTS

1. Field of the Invention
2. Background of the Invention
   2.1 Phospholipids
   2.2 Phospholipid Purification
3. Summary of the Invention
4. Brief Description of the Figures
5. Detailed Description of the Invention
   5.1 Partition Coefficient of PC and PE in Mixed Acetonitrile-Hexane Solvent
6. Examples
   6.1 Phospholipid Purification Using Acetonitrile Solvent
      6.1.1 Direct Extraction of Phospholipids from Egg Yolk Using Acetonitrile
      6.1.2 Direct Acetonitrile Extraction of Phospholipids from Acetone-Washed Egg Yolks
      6.1.3 Purification of Egg Yolk Derived PC with Acetonitrile After Initial Extraction of Phospholipids by Conventional Methods
      6.1.4 Removal of Egg Yolk Neutral Lipids by Supercritical $CO_2$ Before or After Extraction With Acetonitrile
   6.2 Phospholipid Purification at Different Scale Levels and Using Countercurrent Extraction
      6.2.1 Large Scale Purification of Phosphatides from Chicken Egg Yolks
      6.2.2 Microgram and Milligram Scale Countercurrent Purification of Egg Yolk Derived PC and PE
      6.2.3 Gram Scale Purification of Egg Yolk Derived PC and PE
      6.2.4 Gram to Kilogram Scale Purification of Egg Yolk Derived PC and PE by Extraction Using Packed Column Method
      6.2.5 Pilot Plant Scale Purification of Egg Yolk Derived PC and PE by Extraction Using Countercurrent Reciprocating Plate Karr Column

1. FIELD OF THE INVENTION

The present invention relates to a process for the production of high-purity, individual phospholipids from mixtures thereof, by means of separation techniques utilizing solvents novel for this purpose. More specifically, this invention concerns a process for separating and purifying phospholipids, especially those of the sub-class of phosphatides, including, but not limited to the variant fatty acid chain members of the phosphatidylcholine ("PC") or lecithin, phosphatidylethanolamine ("PE"), phosphatidylserine ("PS") and phosphatidylglycerol ("PG") groups.

Particular embodiments of this invention incorporate various known solvent-based separation methods using the solvent systems here disclosed to be most effective in this novel application. Specific phospholipids can be extracted in high purity from mixtures of phospholipids derived from egg yolks, soya beans or other sources because of the different degrees of solubility of the phospholipids in the solvent used. This invention teaches the novel use of a solvent selected from the group consisting of acetonitrile, and mixtures of acetonitrile and one or more hydrocarbons of the group consisting of pentane, hexane, isohexane, heptane and octane, and mixtures of hydrocarbons such as petroleum ether or mixtures of acetonitrile and fluorocarbons.

The present invention is advantageous in that it is both less time consuming and less costly than other known methods.

2. BACKGROUND OF THE INVENTION

2.1 Phospholipids

Phospholipids, including PC, which is commonly known as lecithin, are members of the class of phosphatides. They are of significant commercial importance because of their wetting and emulsifying properties. They are widely used as ingredients in food products, cosmetics, pharmaceuticals, insecticides, paints, plastics and textiles, and have also found numerous applications in the petroleum industry. Because of its widespread occurrence in nature, PC is known colloquially as "nature's emulsifier." The occurrence of PC as a component of cell membranes has been the subject of much recent scientific research. Emphasis in this research has been on the determination of the physical properties and functional characteristics of PC.

Purified egg phospholipids are currently used as a starting material to synthesize other compounds such as glycerophosphocholine; saturated, unsaturated, single and mixed fatty acids, phosphatidylcholines, phosphatidylethanolamines, phosphatidylglycerols, phosphatidylserines, phosphatidic acids, and diether lipids, etc.

2.2 Phospholipid Purification

At present, high purity PC is typically obtained by time consuming, expensive methods such as high pressure liquid chromatography (HPLC), solid-liquid column chromatography (SLCC), flash chromatography, and thin layer chromatography (TLC).

These methods involve the separation of the lipids, typically by solvent extraction or by other solvent-based techniques. Neutral lipids can be separated from the phospholipid class by precipitation with cold acetone. A form of chromatography is then used to separate the individual lipid components. HPLC and flash chromatography on silica gel or alumina represent the state of the art in chromatography. For example, Jungalwala et al. [Biochem. J. 155: 55 (1976)] have described HPLC in silica-gel, using a mixture of acetonitrile, methanol and water as eluant, to separate phosphatidycholine from sphingomyelin. These methods, because they are relatively faster than conventional column chromatography, permit higher solvent flow-rates through the column (throughput) than are attainable with slow conventional column chromatography. Chromatographic means are, however, generally slow and costly. On a large scale, especially, the large quantity of column packing required and the high associated instrumentation costs limit the use of column chromatography to the separation and purification of only the most valuable and expensive compounds.

U.S. Pat. No. 2,651,646, issued to Goldsmith, discloses a method of purifying monoglycerides from diglycerides, using multiple solvent systems including methanol-hydrocarbon, methanol-water-hydrocarbon, and ethanol-water-hydrocarbon. These systems, however, do not exhibit highly selective solubilization characteristics towards phospholipids, as do the acetonitrile and acetonitrile-hydrocarbon mixtures taught in this invention. Other solvent systems, such as ethylene glycol-hydrocarbon, tested in the course of research leading to this invention, also lacked the discovered selective solubilization characteristics of the acetonitrile and acetonitrile-hydrocarbon solvents.

Another purification approach that has been taken, and one which avoids the toxicity and flammability problems associated with many organic solvents, involves the use of supercritical fluids, especially supercritical $CO_2$. A supercritical fluid is produced by subjecting certain gasses to pressure and temperature conditions such that the gas exists in a high density state and has in general the flow properties of gasses, but cannot assume a true liquid form. In an appropriate system, supercritical fluids such as supercritical $CO_2$ can be used for extraction and purification purposes. For example, in U.S. Pat. No. 4,367,178 Heigel and Hueschens disclose the use of supercritical $CO_2$ in an extraction system to remove oily components from crude soy lecithin preparations, thereby obtaining partially purified lecithin.

3. SUMMARY OF THE INVENTION

Alternate means of phospholipid purification have been investigated, and methods developed based on the discovery of the unique differential solubility properties of acetonitrile, acetonitrile-hydrocarbon mixtures and acetonitrile-fluorocarbon mixtures towards phospholipids, especially as to the separation of PC and PE from other phosphatides and from one another. The novel process of this invention may be used on either the laboratory or the industrial scale. It represents a simple, efficient, rapid and economical means of producing purified phospholipids, particularly PC and PE. The process of this invention readily permits the achievement of greater than 90% pure components. Purities greater than 98% can also be attained without significant additional difficulty. This invention enables the production of large quantities of high purity phospholipids which are needed for the preparation of pharmaceuticals. The large volume of high purity phospholipids that can be easily and cheaply produced via the process of this invention will also permit their broader use in other commercial applications where less pure preparations have heretofore sufficed, thus resulting in concommitant improvements in the quality of those products.

The process of this invention eliminates the use of column chromatography for the purification of PC and PE derived from egg yolks and for the partial purification of PC, PE, PS, PG and cardiolipids ("CL's") from other sources. Separation and purification of phosphatides from sources other than egg yolks or soya beans may be less complete because other source materials may contain more complex mixtures of phosphatides which increases the difficulty of separation.

The process of this invention is based on multiple solvent extractions performed sequentially using acetone or supercritical $CO_2$, chloroform-methanol and acetonitrile or acetonitrile-hydrocarbon solvents. These extractions take advantage of the solubility differentials of phospholipids in these solvents. By altering the number of the extraction steps, a purification scheme can be designed that is best suited to the phospholipid mixture in question and the ultimate degree of separation and purity desired.

Equipment such as extractors, filter units, evaporators, crystallization vessels or countercurrent liquid/liquid extraction devices can be employed herein. These are state of the art unit operations currently used throughout the industry. Estimations show that the capital costs for these methods are less than for chromatographic methods for the purification of egg yolk derived PC and PE.

The PC obtained is as pure as that obtained by conventional column chromatography. The system operating parameters, such as the sequence of steps, the quantity of solvents used, and the temperature, can be varied to obtain a range of PC purities. The desired degree of purity depends on such factors as the ultimate use of the PC and cost limitations.

The methods here taught are suitable for phospholipid purification at all scales—from the milligram level to tens-of-Kgs per hour, that is, from laboratory scale to industrial quantity.

4. BRIEF DESCRIPTION OF THE FIGURES

Figure 2:
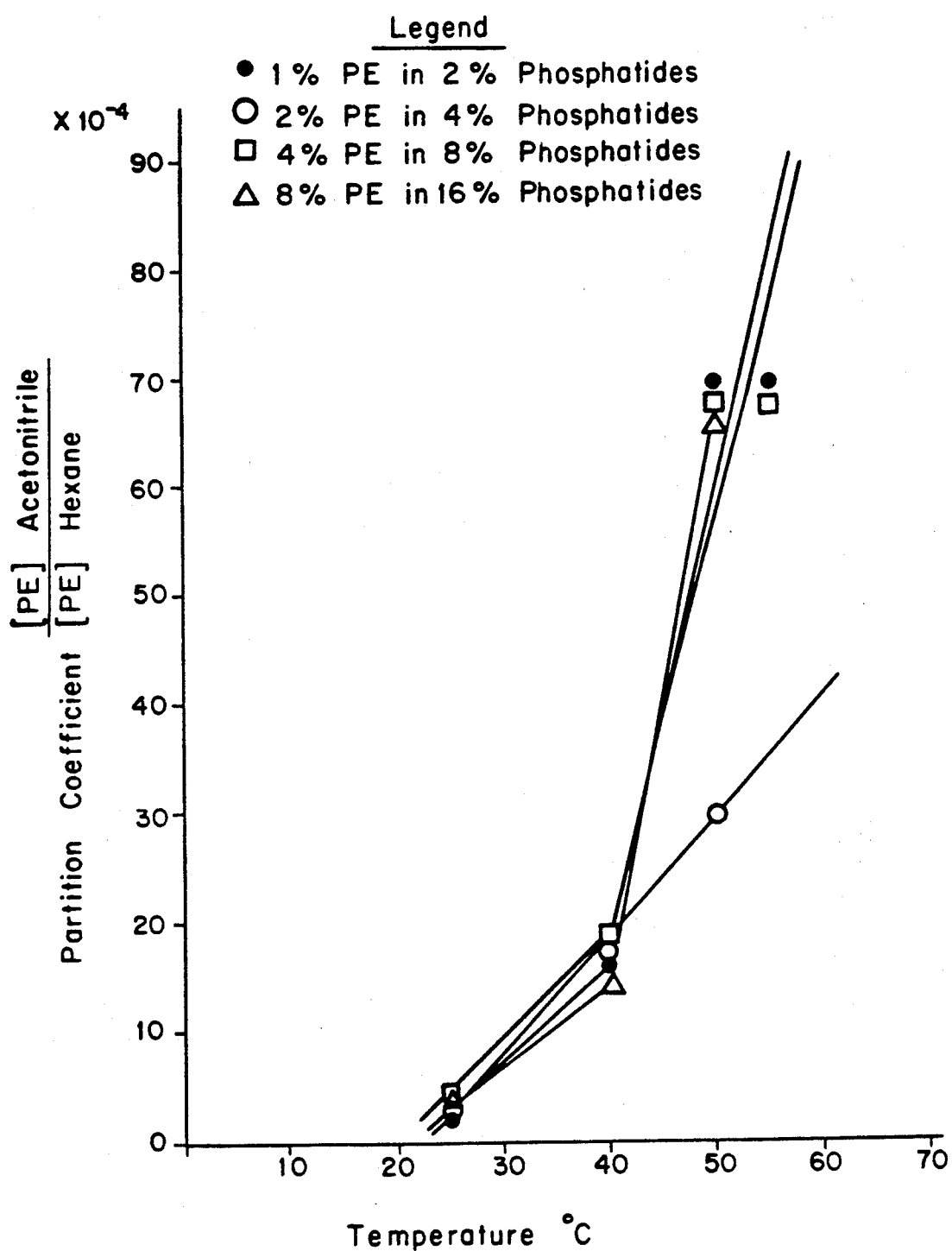
Figure 3:
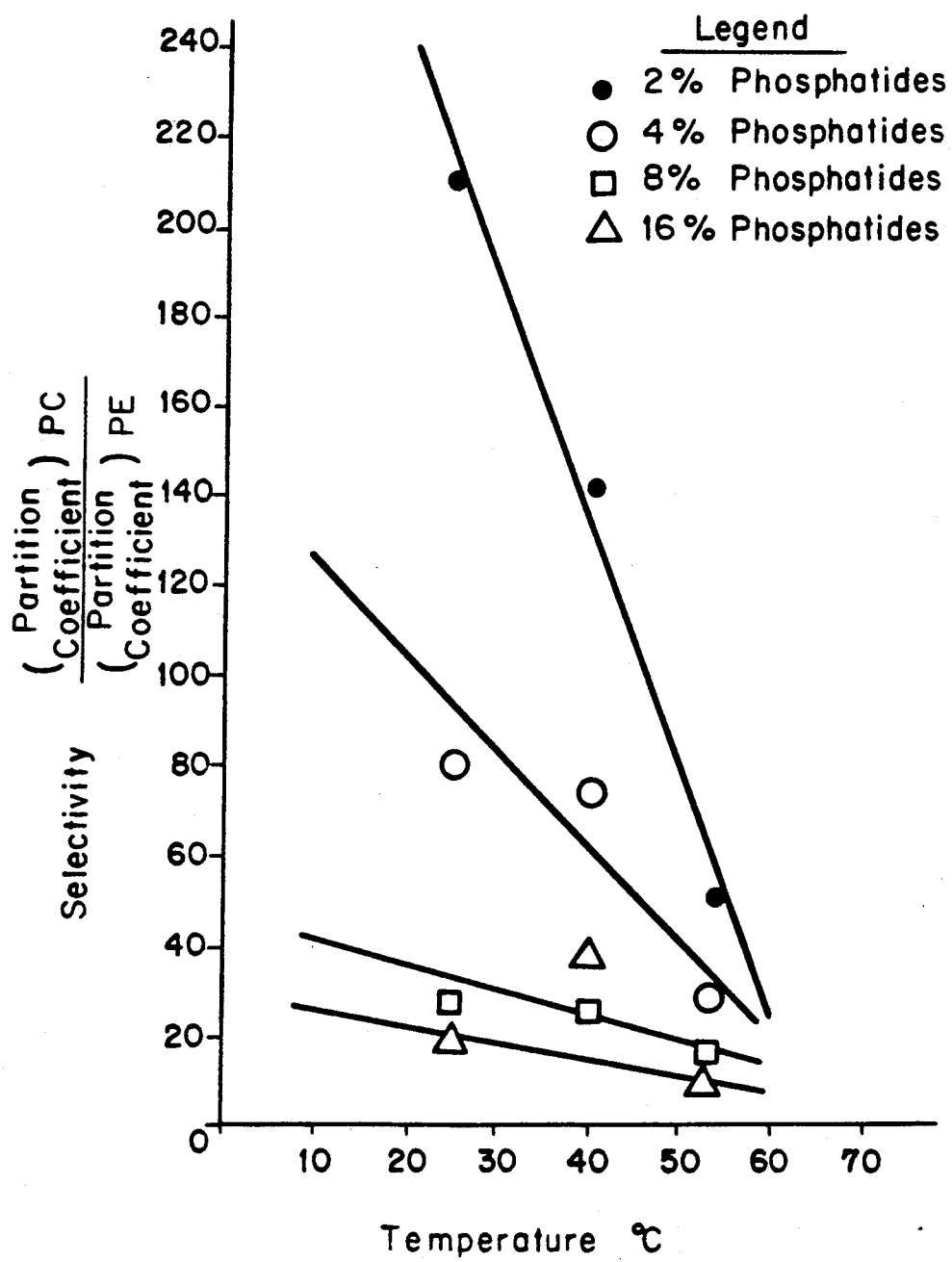

The present invention may be more readily understood by reference to the following figures, wherein FIG. 1 is a graphical representation of the temperature dependency of the partition coefficient of PC in an acetonitrile-hexane system;

FIG. 2 is a graphical representation of the temperature dependency of the partition coefficient of PE in an acetonitrile-hexane system; and FIG. 3 is a graphical representation of the selectivity of PC over PE in the acetonitrile phase of an acetonitrile-hexane system, expressed as a function of temperature.

5. DETAILED DESCRIPTION OF THE INVENTION

This invention is based on the discovery of the unexpected selective solubility differences of phospholipids such as PC and PE, the major groups of phospholipids, in acetonitrile. For purposes of illustration, embodiments of the invention as applied to the purification of egg yolk derived PC and PE are herein described. Egg yolk derived PC has a limited solubility in acetonitrile at room temperature (2 grams/liter), while egg yolk derived PE is practically insoluble in this solvent at room temperature.

In accordance with the present invention, PC and PE of highest purity are readily and economically isolated from a mixture of phosphatides using acetonitrile and/or an acetonitrile-hydrocarbon solvent system or an acetonitrile-fluorocarbon solvent system. The preferred source material for mixtures of phosphatides in the present invention is egg yolks or soya beans. Such source material provides a mixture of phosphatides consisting primarily of PE and PC. The use of other source material, such as plant or animal tissue extracts, is within the scope of this invention; however, some sources yield complex mixtures which increase the difficulties of purifying the individual phosphatides. It has now been discovered that acetonitrile preferentially extracts PC, whereas PE, being insoluble in acetonitrile, remains in the hydrocarbon phase of the two-solvent system. Extraction with acetonitrile or an acetonitrile-hydrocarbon solvent system can be employed in various separation techniques which are based upon the solubilities and/or the partition coefficients of the solutes. The countercurrent distribution method is the method of choice for achieving the highest purity in the separated phosphatides.

The starting material of the process herein is a mixture containing PC and one or more other phosphatides of the group PE, PS, PG, CL, sphingomyelins (SPLs) and phosphatidic acid (free form).

The starting material of the present invention is preferably obtained from egg yolks or soya beans since, in addition to the reasons indicated earlier, they are readily available and inexpensive. The source materials can be treated with any known methods to remove extraneous substances which might hinder the purification of the phosphatides, such as proteins, carbohydrates, and neutral lipids (NLs).

In a typical composition of hen's egg yolk, the dry weight consists of 15% PC, 40% NLs, and 5% PE, and the rest of the components comprise proteins and carbohydrates.

Although this invention discloses several possible protocols for the purification of PC and/or PE from egg yolk, all methods are based on the discovery of acetonitrile's unique solubility properties toward phospholipids.

It is especially important to first remove substances from the source or starting material which easily partition into acetonitrile and, consequently, would raise the impurity level of the end-product. For instance, some NLs contained in egg yolks easily partition into acetonitrile. Therefore, NLs and pigments, such as color carotenoids and cholesterol, may be first removed from the source material in accordance with the present invention through a sequence of extractions which includes precipitation with cold acetone, extraction with a mixture of one of the paired solvents of the group methylene chloride-methanol, methylene chloride-ethanol, hexane-methanol, hexane-ethanol, trichlorofluoromethane-ethanol, chloroform-methanol, or ethanol-diethyl ether, or ethanol or methylene chloride alone and precipitation with a mixture of hexane-acetone. Alternatively, a dry egg yolk preparation or the oily residue from the extraction of egg yolks with chloroform-methanol or with one of the other solvents could be extracted with supercritical $CO_2$ instead of acetone to remove the NLs and pigments.

According to the invention, the phosphatides can be first dissolved in an organic solvent, such as hexane, and the PE precipitated with acetonitrile, or they can be directly extracted with acetonitrile. After evaporation of the acetonitrile solvent, the remaining phospholipid residue contains the PC in a sufficiently pure state. Any NLs, if still present, can be removed by precipitation with acetone to achieve even greater purity PC. The PC so prepared is greater than 95% pure with less than 2% PE present.

The egg yolk can be extracted or first dried and washed with cold dry acetone or extracted with supercritical $CO_2$. These extraction steps are well known procedures which remove a large part of the NLs from the egg yolk solids, leaving most of the phospholipids. According to the invention, the residue can then be exhaustively washed with acetonitrile which will extract the PC, leaving insoluble PE. The preparation containing the PC can then be freed of any remaining NLs by precipitation of the PC with acetone from a hexane or chloroform solution of the residue containing the PC and NLs.

Alternatively, the egg yolk, preferably in dried form, may be directly exhaustively extracted with acetonitrile. The acetonitrile extract is then evaporated to dryness and the residue, consisting mostly of PC and NLs, is washed with acetone several times or extracted with supercritical $CO_2$ to remove the NLs.

To obtain PC and PE of greater purity, the phosphatide mixture (prepared according to the first protocol) is first dissolved in a suitable hydrocarbon solvent, preferably hexane. The solute concentration can vary over a broad range, but the most advantageous results are achieved when the solute concentration is within the range of about 0.5 to about 20 grams of solute per 100 mL of solvent, with the preferred embodiment containing an amount of solute of 2 g/100 mL of solvent when operating between 20°-25° C. A higher solute concentration can be maintained at higher temperatures.

Before partitioning the PC from a phosphatide mixture, the acetonitrile and hydrocarbon are desirably preequilibrated in accordance with the present process to reduce the loss of the hexane phase. However, such preequilibration is not necessary to obtain satisfactory results.

Any known separation procedures utilizing the variant partition coefficients of PC and PE in acetonitrile-hydrocarbon or acetonitrile-fluorocarbon are within the scope of the present invention. It is, however, preferable to use multiple extraction techniques to obtain significant quantities of PC.

5.1. Partition Coefficient of PC and PE in Mixed Acetonitrile-Hexane Solvent The partition coefficient of PC in acetonitrile-hexane solvent is a function of both temperature and total phosphatide concentration. The linear temperature dependency of the partition coefficient is clearly shown in FIG. 1. As the temperature is increased, the coefficient increases, indicating an increased amount of PC in the acetonitrile phase. The partition coefficient decreases, however, as total phosphatide concentration increases, indicating the PC:PC molecular interaction in the hexane layer.

PE, on the other hand, has a much lower partition coefficient in acetonitrile-hexane solvent, as shown in FIG. 2. Although the partition coefficient shows a direct linear relationship with temperature, as in the case of PC, there is very little, if any, measurable concentration dependence on the partition coefficient for PE.

This difference in partition coefficients enables one to calculate the selectivity of PC over PE in the acetonitrile phase. FIG. 3 shows an inverse relationship between selectivity and temperature. Selectivity is highest at lower phospholipid concentrations at a given temperature. An approximately 2% phosphatide system at 25° C. demonstrates a high selectivity, over 200, favoring the distribution of PC over PE in the acetonitrile phase.

Once the partitioning of the phosphatides is complete, the acetonitrile can be readily removed by methods known to those skilled in the art, such as by evaporation under vacuum to reduce the boiling temperature and minimize thermal decomposition of the PC. The PC so obtained is sufficiently pure to be used as such, or it can be further purified by redissolving in a minimum amount of hexane and precipitated with cold acetone to remove any traces of NLs. In accordance with this process, a product having a purity greater than 98% can be obtained.

In a preferred embodiment, the evaporation of the acetonitrile is stopped before all of the solvent has been removed. As evaporation proceeds, the limited solubility capacity of the diminishing volume of acetonitrile for PC causes PC to oil out. It has been found that a PC preparation containing less contaminating PE can be obtained by isolating the oiled-out fraction before the evaporation of the acetonitrile is complete. The amount of acetonitrile that must be evaporated is dependent upon the quantity of PC present but typically ranges from about 75 to about 95% of the initial volume. Where more PC is present, less acetonitrile need be removed before the PC begins to oil out, and vice-versa.

In any event, the PC ultimately obtained by this method contains less contaminating PE than does PC from the process wherein all of the acetonitrile is removed, although in either case the percentage of PC in the product exceeds 95%. For this reason, the workup of an oiled-out phase is preferred for any of the processes herein described in which a process step involves the evaporation of acetonitrile from a PC solution.

The differences in partition coefficients are sufficient to yield high purity PC after one extraction. The absolute quantity of PC extracted into the acetonitrile per run is, however, low and multiple extractions and/or excess amounts of acetonitrile are normally required before a significant percentage (i.e., about 50% or greater) of the PC originally present in the sample are transferred from the hexane phase. A number of multiple extractions, on the order of five to thirty, and an excess of acetonitrile of about ten to twenty times the volume of hexane are particularly advantageous embodiments of the procedure.

The operating temperature may vary over a wide range, however, the most advantageous results are achieved when the temperature is within the range of about 0°-65° C., preferably 25°-40° C. The process may be utilized at a higher temperature, when under pressure in a continuous extraction mode. At higher temperatures, however, care must be taken to minimize the decomposition of PC by limiting the time that it is exposed to temperatures greater than about 50° C. This can be achieved in several ways, either by limiting the amount of oxygen present in the system, by maintaining the process in a dark environment, or by the addition of small amounts of antioxidants such as butylated hydroxytoluene or tocopherols or a combination thereof.

6. EXAMPLES

The following examples serve to illustrate specific embodiments of the present invention but do not limit the scope thereof.

6.1 Phospholipid Purification Using Acetonitrile as Solvent

6.1.1 Direct Extraction of Phospholipids from Egg Yolk Using Acetonitrile

Ten egg yolks from Grade A large hen eggs (total weight 200 g), after lyophilization or nitrogen-drying to remove water, are subjected to extraction with one liter of acetonitrile in a Soxhlet extractor to extract the contained phospholipids. Because the normal boiling point of acetonitrile is 80° C., and since the extracted phospholipids should not be subjected to such high temperatures to avoid thermal decomposition, the system should be under vacuum so that acetonitrile can be vaporized at a temperature below 50° C., preferably 40° C. A Buchi Rotoevaporator Model EL-130 equipped with a Soxhlet extractor (500 mL capacity) is suited for laboratory use.

After one hour or more of reflux and after the equivalent amount of acetonitrile cycling through the extractor exceeds 20 liters, the unit is put in distilling mode with a vacuum ranging from 10 mm Hg to such reduced system pressure that allows the acetonitrile to boil at a temperature below 40° C. The residue of the evaporated acetonitrile, 50 g, 68% NLs, 30% PC, 1% PE is dissolved in 100 mL of hexane by warming the mixture to 40° C. to expedite dissolution, whereupon, 2 liters of dry acetone are added. The mixture is warmed until a solution is formed. The solution is then filtered and cooled to 4°-8° C. and maintained at 4°-8° C. for 12 hours, with stirring. The solution is filtered with suction in a Buchner funnel. The filter cake is washed with cold fresh acetone (200 mL) and pumped dry in a dessicator under vacuum (10 mm Hg) yielding a residue of 15-20 g. The residue is redissolved in 50 mL of hexane and precipitated with 1 liter of cold acetone as above, to obtain a sample of egg derived PC weighing 10 grams, at greater than 95% purity.

Alternatively and preferably, the purification procedure may be stopped before all of the acetonitrile has been removed, and an oiled-out fraction may be recovered and processed to obtain an even more pure PC preparation (see Section 5). In a typical run, when about 500 mL of acetonitrile remain in the rotoevaporator unit, an oiled-out fraction weighing about 45 g may be present.

This fraction may be removed and dissolved in 100 mL of hexane by warming the solution to 40° C., at which point 4 liters of dry acetone are added. The warm solution is then filtered hot and cooled slowly to 4°-8° C. and maintained at that temperature for 12 hours with stirring. The solution is then filtered under reduced pressure in a Buchner funnel, and the filter cake is washed with 200 mL of cold acetone and dried in a dessicator under a 10 mm Hg vacuum. The result is a 15-20 g residue which is redissolved in 50 mL of hexane and precipitated with 1 liter of cold acetone as described above. A PC sample weighing about 9 g with a purity of greater than 95% may thus be obtained.

Similar treatment of an oiled-out fraction before complete removal of the acetonitrile in Section 6.1.2 below is also preferable.

6.1.2 Direct Acetonitrile Extraction of Phospholipids from Acetone-Washed Egg Yolks Ten egg yolks (total weight approximately 200 g on a wet basis or, approximately 100 g on a dry basis) are blended in a Waring blender or homogenized in a Polytron homogenizer (Brinkman) with 400 mL of dry acetone at room temperature, cooled to 0°-5° C. for 4 hours and filtered with suction in a Buchner funnel with 2 Wattman Nbl papers; the filtrate is discarded. The filter cake is again blended or homogenized, as above, with 500 mL of dry acetone, the mixture is cooled to from −10° to −5° C. for 2-24 hours, filtered as before and the filter cake dried in vacuo. The residue is placed, as above, in a Soxhlet extractor and the PC is extracted under vacuum with an equivalent 1-50 liters, preferably 20 liters, of acetonitrile for 1-20 hours at 10 mm of Hg and at a bath temperature of 40° C. The residue of evaporation of the acetonitrile (12 g) is dissolved in 20 mL of hexane and precipitated with 400 mL of acetone, as described above, yielding a sample of PC weighing 10 grams, at greater than 95% purity.

6.1.3 Purification of Egg Yolk Derived PC with Acetonitrile after Initial Extraction of Phospholipids by Conventional Methods Ten egg yolks (total weight approximately 200 g, wet basis) or the dry powder therefrom, (total weight approximately 100 g) are first washed twice with two 400 mL portions of dry acetone, as described in Example 6.1.2. The phospholipids are then extracted from the resulting pellet with two 250-mL portions of a mixture of chloroform-methanol solvent in a 1:1 volumetric ratio, at room temperature using mechanical mixing or homogenizing. The mixture is filtered in a Buchner funnel with suction and the filtrate is placed in a separatory funnel to which 225 mL of water is added to form a biphasic system. The flask is gently swirled and the phases allowed to separate. The lower chloroform phase is roto-evaporated to dryness under vacuum of 1 mm Hg at 35° C., carefully avoiding foaming. The residue (approximately 25 g) can be treated in either of two ways:

1) By acetone precipitation, as above (i.e., dissolved in 40 mL hexane and precipitated with 800–1000 mL of cold acetone at from 0°–5° C.). This fraction contains the phosphatides. Its approximate composition is typically 70% PC; 15% PE; 5% NLs; 5% PS; and less than 1% lyso-PC (if the eggs are fresh). These phosphatides can be dissolved in a hydrocarbon and placed in a countercurrent extraction device using acetonitrile as the counter-solvent, as described below. Alternatively, the phosphatides may be dissolved in hexane (30 g phosphatides per 100 mL solvent). This solution is then mixed with 4 liters of acetonitrile. The PE, and approximately ⅔ of the PC separates out of the solution as an oil (oils-out of solution). The acetonitrile upper layer or supernatant, containing the PC, is then evaporated to dryness. The residue (15 gm) is dissolved in 20 mL of hexane and precipitated with 400 mL of acetone. The yield is 10 grams of PC at greater than 95% purity.

2) Alternately, the residue remaining after chloroform evaporation, above, may be extracted with acetonitrile (40 g in 2000 mL) with homogenization, or it may be redissolved in hexane and extracted with 4 liters of acetonitrile, as described above, and further purified by acetone precipitation.

6.1.4 Removal of Egg Yolk Neutral Lipids by Supercritical $CO_2$ before or after Extraction with Acetonitrile To avoid the use of acetone as a means of removing neutral lipids, either of the following methods based upon the use of supercritical $CO_2$ may be employed.

In one embodiment of the invention in which acetonitrile extraction is carried out first, 12 yolks from Grade A large hen eggs are lyophilized to produce about 110–130 g of dried material. This material is then extracted with 2 liters of acetonitrile in a Buchi Model El-130 Rotoevaporator equipped with a Soxhlet extractor. The system is operated under reduced pressure at 10–50 mm Hg at a bath temperature of from about 10° to about 50° C., preferably 40° C. After 12–15 hours of extraction, the unit is put in the distillation mode and the acetonitrile is evaporated down to a volume of about 500 mL. An oiled-out fraction weighing about 46 g is then removed.

Twenty grams of the oiled-out layer (which in a representative run contained about 68% NLs, 30% PC and 0.1–1% PE) is placed in a supercritical $CO_2$ extracting unit and extracted at a presure above 1,071 pounds per square inch (psi), preferably at 5,000 psi and at a temperature above 31° C., preferably at 40° C., at which point the supercritical $CO_2$ has a density of about 0.94 g/mL. The flow rate through the system is maintained at about 0.1–1 liters/minute, with a total supercritical $CO_2$ to oiled-out sample ratio of from about 100 to 200, preferably 150. Preferably, from about 1 to about 5 percent ethanol may be added to the supercritical $CO_2$. The added ethanol renders the supercritical $CO_2$ more polar, thereby improving cholesterol extraction. About 4.5 g of residue, which typically contains more than 95% pure PC, with about 0.2% PE and 1.2% cholestrol, can be removed from the extractor once extraction is complete.

In another embodiment in which supercritical $CO_2$ extraction precedes acetonitrile extraction, 10 g of lyophilized egg yolk powder are extracted with the $CO_2$ at a temperature above 31° C., preferably at 40° C. and at a pressure above 1,071 psi, preferably at 5,000 psi, with a flow rate of 75 g of $CO_2$ per minute. The eluant is monitored at 205 nm, and the extraction is stopped after the absorbance falls below 0.1 O.D. units. The extract, typically containing about 3 g of oil (triglycerides and cholesterol), is discarded. The remaining residue which generally weighs about 5.3 g, is extracted with two 50-mL portions of chloroform-methanol (1:1), at which point 45 mL of water are added to the combined extracts to form a biphasic system, and the lower chloroform layer is evaporated to dryness.

The resulting residue is dissolved in 100 mL of hexane, placed in a separatory funnel and extracted with fifteen 100-mL portions of acetonitrile that has been pre-equilibrated with hexane. The combined acetonitrile extracts are then evaporated down to a 25–50 mL volume, and the oiled-out fraction is removed and dried in a dessicator. This procedure typically yields about 1.6 g of residue which contains more than 95% PC. Contaminants generally consist of less than 1% PE, 0.5% triglycerides and 0.5% cholesterol.

6.2 Phospholipid Purification at Different Scale Levels and Using Countercurrent Extraction

6.2.1 Large Scale Purification of Phosphatides from Chicken Egg Yolks

The fresh yolks of 60 jumbo eggs (total weight approximately 3600 g) are thoroughly blended with 2 liters of dry acetone at 2° C. to form a suspension. The resulting suspension is cooled for 2 hours at 4°–8° C., and then alternately centrifuged at 0°–4° C. for 10 minutes at 8000 rpm (9000×g) or filtered with suction in a Buchner funnel.

The resulting pellet or filter cake is re-suspended in 2 liters of dry acetone at 2° C. and the above cooling and centrifugation or filtering steps are repeated.

The resultant mixture is then filtered with suction and the precipitate dried in a rotary evaporator under reduced pressure to remove any residual acetone.

The egg yolk derived phospholipids are further extracted in three stages with a total of 2 liters of chloroform and methanol (1:1 volumetric ratio) divided into 3 equal portions. To the combined extracts, 900 mL of water are added to form a biphasic system. After allowing this extraction mixture to stand for 15 hours, the lower chloroform phase is removed and carefully dried in a rotary evaporator to obtain a milky residue.

The residue is dissolved in 200 mL of hexane, to which solution 4 liters of hot dry acetone at 60° C. are added. The solution is stirred, cooled to 4° C., and maintained at this temperature for 2-4 hours. The mixture is then filtered with suction. The above procedure is repeated with the filtered precipitate, yielding 87 grams of phosphatides containing 52.3% PC, 44.7% PE, 2% NLs, 0.5% PS, and 0.5% SPLs.

6.2.2 Microgram and Milligram Scale Countercurrent Purification of Egg Yolk Derived PC and PE In a 15 mL centrifuge tube, approximately 50 mg of egg yolk derived phosphatides (52% PC), as obtained in Example 6.2.1, are dissolved in 5 mL of hexane, to which 5 mL of acetonitrile are added. The tube is stoppered and shaken vigorously at 25° C.

Upon separation of the phases after 1 minute, the lower phase containing acetonitrile is removed from the centrifuge tube using a Pasteur pipette. The volume of hexane is brought back up to 5 mL, and 5 mL of acetonitrile are added for another extraction. (Note: It is preferable to equilibrate the two phases prior to use.) A total of five extractions are performed.

The extract from the individual extractions is combined and dried in a rotary evaporator to yield a total weight of recovered product of 17.6 mg (68% yield).

The combined extract is then diluted in a mixture of 0.4 mL hexane, isopropanol and water in the proportions 60:50:8 parts by volume, and analyzed by high-pressure liquid chromatography (HPLC) for purity. Analysis shows a purity of greater than 98% PC at an absorbance peak at 205 nM.

6.2.3 Gram Scale Purification of Egg Yolk Derived PC and PE

Five g of egg yolk derived phospholipids, containing 52% PC, 45% PE, 2% NLs, 0.5% PS and 0.5% SPLs, are dissolved in 500 mL of distilled hexane and placed in a one-liter separatory funnel. Twenty aliquots, each of 250 mL of distilled acetonitrile, equilibrated with hexane, are used consecutively to extract the phospholipids from the hexane layer. After addition of each aliquot, the mixture is thoroughly mixed by shaking or stirring and partition of the layers is allowed to occur. The lower acetonitrile layer from each extraction is removed and combined. The extract from the first wash, however, is often kept separate, as it contains a large pecentage of NLs. The combined extracts from the other extractions are reduced to dryness by rotary evaporation under vacuum (2 mm Hg). Product yield after 10 extractions is 1.2 grams; after 20 extractions, 2.1 grams. The dried residue consists of greater than 90% PC, 0.5% PE, 0.5% PS, traces of SPLs and approximately 9% NLs as measured by HPLC, at an absorbance peak at 205 nM.

The 2.1 g of residue are dissolved in 5 mL of chloroform, to which 60 mL of hot dry acetone are added. The hot solution is filtered and cooled slowly to 0° C. with stirring. A white amorphous precipitate is formed, which is recovered by filtration or centrifugation at 0° C., washed with fresh ice-cold, dry acetone, and dried under vacuum. The product, 1.8 g at a yield of 69%, is pure as measured by TLC. HPLC analysis at an absorbance peak at 205 nm shows the product to be 97.5% pure PC with 1% PE, 1.5% NLs and a trace of SPLs. The hexane layer, consisting of greater than 70% PE and approximately 19.5% PC is also an enriched source of PE.

6.2.4 Gram to Kilogram Scale Purification of Egg Yolk Derived PC and PE by Extraction Using Packed Column Method A glass column (5×50 cm), equipped with a lower teflon (TM) stopcock, a sintered glass disc just above, and one liter of ¼ cm ceramic saddles, is filled with 500 mL hexane containing 5 to 10 g of egg yolk derived phosphatides (52% PC, 45% PE, 2% NLs, 0.5% PS and 0.5% SPLs) layered on 200 mL of acetonitrile. A second sintered glass disc is placed at the top of the column and acetonitrile is layered above the disc in a glass reservoir. By opening the bottom stopcock, the acetonitrile is allowed to flow through the column at a controlled rate of approximately 20 mL per minute. Faster flow rates may be used as long as the dispersed mobile acetonitrile phase does not coalesce. Twelve 1-liter fractions are collected and evaporated to a small volume under reduced pressure at 40° C. Fractions 2-12 are then combined and dissolved in 5 mL of chloroform, to which 80 mL of hot dry acetone are added. The hot solution is filtered at 60° C. and cooled slowly to 0° C. with stirring over 1 hour. After 3 hours, the resulting precipitate is filtered, washed with 20 mL of ice-cold acetone, and dried under vacuum. The 2.5 grams of PC product contain 1.3% NLs, with a trace of SPLs.

6.2.5 Pilot Plant Scale Purification of Egg Yolk Derived PC and PE by Extraction Using Countercurrent Reciprocating Plate Karr Column A feed solution containing 2% egg yolk-derived phosphatides in hexane is pumped into a 12 foot long, one-inch diameter reciprocating Karr column (Chem-Pro Corp., Fairchild, N.J.) at a rate of 1 liter per hour at a position approximately one-third from the bottom of the column (i.e., four feet from the bottom of the column). Acetonitrile extraction solvent is pumped into the top of the column at a rate of 12 liters/hour. A small amount of hexane wash solvent is pumped into the bottom of the column at a rate of 55 mL per hour. The eluted PC-rich acetonitrile extract is collected at the bottom of the column while the PE-rich hexane raffinate is eluted at the top. The agitation rate of the reciprocating plates is adjusted until flooding of the column occurs. The rate is then reduced slightly. This optimum rate provides maximum efficiency of mixing, separation, and extraction at a maximum number of plates in the instrument. The hexane and acetonitrile solvents should be equilibrated together before use. The solvent flow rates may be varied over a wide range, depending on the column design, to optimize capacity and product purity parameters. The temperature may be varied from 0° to 60° C., or even higher under pressure. The preferable operating temperatures are between 25°-40° C.

The acetonitrile extract is evaporated in a flash evaporator at conditions of less than 40° C. temperature and a pressure of 1.0 mm Hg. Approximately 14 grams of greater than 98% pure PC are collected per hour.

The PC may be further purified to eliminate the NLs by using acetone precipitation, once or twice, by dissolving the resulting fraction in hexane at a rate of from 0.5-1 g/mL and adding a 10-20 fold excess of hot acetone at 60° C. The hot solution is filtered, cooled with stirring to 0°-4° C. and kept at low temperature for 4 hours. The resulting white flocculant precipitate of PC is collected by filtration with suction. The product is greater than 99% pure, as analyzed by HPLC at an absorbance peak at 205 nm, with less than 0.1% PE present. Greater than 90% of the PC in the feed sample may be recovered using this technique. The hexane raffinate from the column is rich in PE, greater than 80% pure.

The PE-rich hexane fraction can be purified of PC by exhaustively extracting it with acetonitrile. The remaining hexane layer is then evaporated to a small volume under reduced pressure and the PE precipitated from a 20 fold excess of acetone. The solution is cooled to 4° C. and filtered with suction. The acetone precipitation step may be repeated if necessary to eliminate the remaining NLs. The PE is greater than 90% pure. Acidic phospholipids, if present, can be removed by DEAE cellulose chromatography or by conventional column chromatography, such as HPLC.

What is claimed is:

1. A process for purifying individual phospholipids from mixtures thereof, which comprises separating phosphatidylcholines from the phospholipid mixtures by non-chromatographic extraction with acetonitrile, comprising:
   (a) extracting phospholipids from egg yolks with acetonitrile;
   (b) evaporating from about 75 to about 95% of the acetonitrile to produce an oiled-out fraction, which fraction is removed from the remaining acetonitrile; and
   (c) extracting the oiled-out fraction with an organic solvent.

2. The method according to claim 1 in which the organic solvent of step (c) is acetone.

3. The process according to claim 1 comprising:
   (a) extracting egg yolks with an organic solvent to form a residue;
   (b) extracting phospholipids from the residue with an organic solvent pair selected from the group consisting of chloroform-methanol, methylene chloride-methanol, methylene chloride-ethanol, hexane-methanol, hexane-ethanol, trichlorofluoromethane-ethanol, and ethanol-diethyl ether;
   (c) adding water to the extract of step (b) to form a biphasic system;
   (d) collecting the organic phase of the biphasic system and evaporating the organic solvent to form a residue;
   (e) dissolving the residue of step (d) in hexane;
   (f) extracting the hexane solution with acetonitrile; and
   (g) evaporating from about 75 to about 95% of the acetonitrile to produce an oiled-out fraction which fraction is removed from the remaining acetonitrile.

4. The method according to claim 3 wherein the organic solvent of step (a) is acetone.

5. The process according to claim 1 comprising the additional steps of extracting the separated phosphatidylcholines with a solvent capable of separating the phosphatidylcholines from neutral lipids and pigments.

6. The process according to claim 1 comprising the additional step of extracting the separated phosphatidylcholine with an organic solvent.

7. A process for purifying individual phospholipids from mixtures thereof, comprising the steps of:
   (a) separating phosphatidylcholines from the phospholipid mixtures by extracting with acetonitrile; and
   (b) extracting the separated phosphatidylcholines of (a) with a solvent capable of separating them from neutral lipids.

* * * * *